(12) United States Patent
O'Mara, Jr.

(10) Patent No.: US 8,506,476 B1
(45) Date of Patent: Aug. 13, 2013

(54) INJECTION DEVICE FOR ENDOSCOPY

(71) Applicant: James Wright O'Mara, Jr., Jackson, MS (US)

(72) Inventor: James Wright O'Mara, Jr., Jackson, MS (US)

(*) Notice: Subject to any disclaimer, the term of this patent is extended or adjusted under 35 U.S.C. 154(b) by 0 days.

(21) Appl. No.: 13/694,030

(22) Filed: Oct. 22, 2012

Related U.S. Application Data

(60) Provisional application No. 61/628,165, filed on Oct. 25, 2011.

(51) Int. Cl.
*A61B 1/04* (2006.01)

(52) U.S. Cl.
USPC ................ 600/117; 606/44; 606/172

(58) Field of Classification Search
CPC ........................................ A61B 1/04
USPC ........... 600/101, 117, 164; 604/117, 170.03, 604/241, 264, 272; 606/44, 46, 172
See application file for complete search history.

(56) References Cited

U.S. PATENT DOCUMENTS

| | | | |
|---|---|---|---|
| 4,425,120 A | 1/1984 | Sampson | |
| 4,710,171 A | 12/1987 | Rosenberg | |
| 4,763,667 A | 8/1988 | Manzo | |
| 4,877,037 A * | 10/1989 | Ko et al. | 600/569 |
| 5,015,235 A | 5/1991 | Crossman | |
| 5,403,288 A | 4/1995 | Stanners | |
| 5,549,558 A | 8/1996 | Martin | |
| 5,665,093 A * | 9/1997 | Atkins et al. | 606/108 |
| 5,807,402 A | 9/1998 | Yoon | |
| 5,860,953 A * | 1/1999 | Snoke et al. | 604/95.04 |
| 5,944,700 A | 8/1999 | Nguyen | |
| 6,560,975 B1 | 5/2003 | Weldon | |
| 6,796,963 B2 | 9/2004 | Carpenter et al. | |
| 6,905,486 B2 | 6/2005 | Gibbs | |
| 6,918,892 B2 | 7/2005 | Martin | |
| 6,926,696 B2 | 8/2005 | Mohammed | |
| 7,258,692 B2 * | 8/2007 | Thelen et al. | 606/62 |
| 7,678,077 B2 * | 3/2010 | Harris et al. | 604/117 |
| 7,909,802 B2 | 3/2011 | Sauter | |
| 2007/0197996 A1 * | 8/2007 | Kraft et al. | 604/500 |
| 2009/0069823 A1 * | 3/2009 | Foerster et al. | 606/139 |
| 2009/0204071 A1 | 8/2009 | Grant | |
| 2009/0270819 A1 | 10/2009 | Vitali | |
| 2009/0326452 A1 | 12/2009 | Alchas | |
| 2010/0094425 A1 * | 4/2010 | Bentley et al. | 623/17.16 |
| 2011/0022006 A1 | 1/2011 | Walters | |
| 2011/0028916 A1 | 2/2011 | Schweikert | |
| 2012/0253392 A1 * | 10/2012 | Bentley et al. | 606/232 |

* cited by examiner

*Primary Examiner* — Laura Bouchelle
*Assistant Examiner* — Gerald Landry, II
(74) *Attorney, Agent, or Firm* — Grace L. Bonner

(57) ABSTRACT

A medical device for injection during endoscopy or arthroscopy, the device having a curved, hollow needle, optionally coated by a semi-rigid covering, all surrounded by a curved tubular sleeve, wherein the needle is attached to a base, separated from the sleeve by one or more removable extensions or tabs, and a connection means for connecting either directly to a syringe for a liquid or semi-liquid treatment or to an extension tube connected to such a syringe.

8 Claims, 1 Drawing Sheet

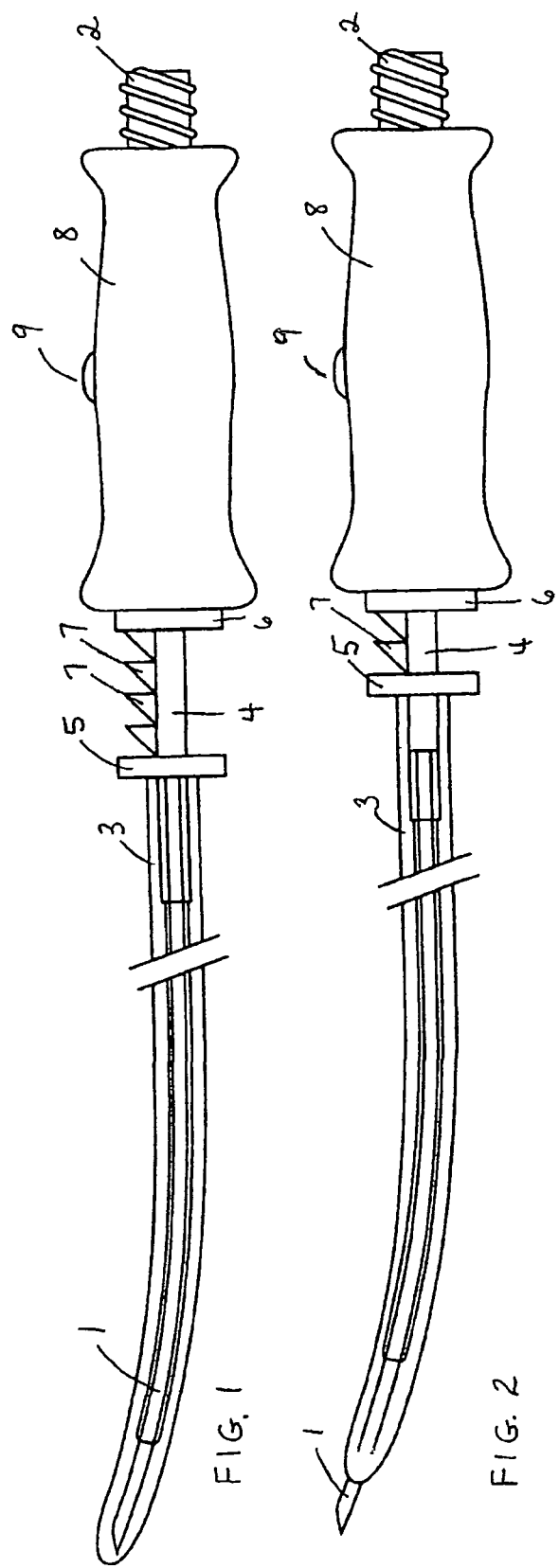

INJECTION DEVICE FOR ENDOSCOPY

BACKGROUND OF THE INVENTION

Arthroscopy (also called arthroscopic surgery) is a minimally invasive surgical procedure in which an examination and sometimes treatment of the interior of a joint or other body cavity is performed using an arthroscope, a type of endoscope that is inserted near or into the joint or other cavity through a small incision. Arthroscopic procedures can be performed either to evaluate or to treat many conditions such as orthopedic conditions, including torn floating cartilage, torn surface cartilage, ACL reconstruction, and trimming damaged cartilage. The surgical instruments used are smaller than traditional instruments. Surgeons view the joint or tissues on a video monitor, and can diagnose and repair or treat the joint or tissue, such as ligaments, menisci or cartilage. It is technically possible to do an arthroscopic examination of almost every joint or other cavity in the human body. The joints that are most commonly examined and treated by arthroscopy are the knee, shoulder, elbow, wrist, ankle, foot, and hip.

Treatments of a joint during arthroscopy include application of a local anesthetic to relieve pain or growth factors or certain blood products to aid in healing. Examples of other surgeries in which treatments of other cavities could be made include laparoscopy and endoscopic sinus surgery. However, the proper placement of these treatments is essential to their safe and effective use. Recently it has been learned that the application of even one effective dose of an anesthetic can damage cartilage cells (chondrocytes), possibly leading to chondrolysis (Chu C R et al: "The in vitro effects of bupivicaine on articular chondrocytes", The Journal of Bone and Joint Surgery (Br), 2008; 90-B:814-20). The FDA has warned physicians that post-surgical intra-articular infusion through the use of pain pump may cause chondrolysis and is not approved. Therefore, it is desirable to limit or avoid the exposure of chondrocytes to local anesthetics, but instead to inject the anesthetic into the soft tissue surrounding the joint such as the capsule or other adjacent soft tissues that are extra-articular.

Treatments to promote healing of tissue damage discovered during arthroscopy include the application of growth factors or blood products (Randelli P S, Arrigoni P, Cabitza P, Vollpi P, Maffulli N: Autologous platelet rich plasma for arthroscopic rotator cuff repair: A pilot study. Disabil Rehabil 2008; 30:1584-1589, Orrego M, Larrain C, Rosales J, et al: Effects of platelet concentration and a bone plug on the healing of hamstring tendons in a bone tunnel. Arthroscopy 2008; 24:1373-1380, Sanchez M, Azofra J, Annitua E, et al: Plasma rich in growth factors to treat an articular cartilage avulsion: A case report. Med Sci Sports Exerc 2003; 35:1648-1652). It would be desirable to be able to place these treatments in the place or places in the joint or tissues where they would be the most effective in promoting healing.

The application of other treatments used in laparoscopy, endoscopic sinus surgery, or other endoscopic surgical techniques would benefit from a device that allows precise and safe application of medication or other medical treatments to remote parts of a body cavity.

The use of intra-articular or extra-articular treatments could be more effectively done during arthroscopy when the tissues are visualized and the application can be directed to the proper place in or around the joint. Likewise, treatments introduced in other cavities during endoscopy may be more effective when precisely applied to the best location for the treatment. The present invention meets the need for a means to apply treatments during endoscopy in such a manner as to reduce the risk of damage from some treatments or to increase the rate or level of healing from other treatments.

SUMMARY OF THE INVENTION

It is an object of this invention to provide an injection device useful in delivering treatments during arthroscopic surgery, the device comprising a curved hollow needle 1, optionally encased in a semi-rigid covering, enclosed in a tubular sleeve 3 being curved to match the needle. The needle 1 is proximally attached to a base 4 which is fitted into or over the proximal end of the sleeve 3. The base 4 is prevented from sliding into or over the sleeve, and thus exposing the needle, by one or more removable tabs 7. The proximal end of the base 4 is fitted with a connection means 2 to allow for delivery of the treatment through the base 4 and the needle 1 to the desired site. The connection means 2 may be used to directly connect the needle to a reservoir for the treatment or to an extension tube connected to such a reservoir. Preferably the reservoir is a syringe that allows for the metered delivery of the treatment.

The length of the needle 1, the sleeve 3, and the base 4 are variable because different joints or tissues will require different proportions of these components for optimal delivery of treatment to the cavity or joint or tissues surrounding it. However, the distance between the proximal end of the sleeve 3 and the proximal end of the base 4 will be relatively small to prevent over-penetration of the needle upon deployment. An exemplary difference is 4 mm.

The device also has a means for stopping the movement of the base into or over the sleeve, i.e., a stop. The stop may be in the form of an annular ridge 5 on the sleeve 3 at its proximal end, with another annular ridge 6 on the base 4. Other structures that would stop the movement can be used, including an optional handle 8 attached to the proximal end of the base 4 or the sleeve 3. There may also be an indication means on the base 4 or the handle 8 to let the user know where the curve of the device is oriented after insertion. The indicator may be a marking or a three dimensional part of the device. An example would be a shape that is inscribed on or raised above the base 4 or the handle 8, such as the bump 9 shown in the figures.

Thus the present invention fulfills a need in the art of endoscopy and arthroscopy by providing a means to reach aspects of a joint or tissue not easily or safely accessed with current devices.

DESCRIPTION OF THE DRAWINGS

FIG. 1 is a side view of an example of the device with the optional handle, according to the invention prior to use, with a portion of the sheath and needle deleted.

FIG. 2 is a side view of the device of FIG. 1 with the needle extended.

DETAILED DESCRIPTION OF THE INVENTION

The present invention is an injection device for use during arthroscopy as a means for delivery of a treatment in or near the joint or during endoscopy as a means for delivery into a body cavity or tissue. To use the device after removal from sterile packaging, it is connected to a reservoir, preferably a syringe, either directly or by means of a connecting tube, wherein the reservoir contains the intended treatment. The device is inserted into the desired location, as visualized by a camera useful for arthroscopy. The tab is removed, or, for an embodiment with more than one tab, the desired number of tabs is removed. The number of tabs to be removed will be dependent on the desired length of needle to extend beyond the sleeve. Alternatively, the tab or tabs may be removed prior to insertion of the device, but it is preferable to remove them after the device has been safely placed near where the treatment is to be delivered before the tab(s) is removed. The device may also be placed within the cavity or tissue prior to connection to a reservoir for the treatment, which would then occur upon accurate placement.

After the device is placed in or near the joint or other tissue being treated and, if still in place, the proper number of tabs is removed, the proximal end of the base is moved toward the proximal end of the sleeve (or vice versa) until stopped by a stopping structure (for example, two ridges 5 and 6, one on the base 4 and one on the sleeve 3, touching each other; or a handle 8; or other means) or blocked by a remaining tab or tabs, if any. The treatment is then deployed through the needle at the desired location. If desired, the device may be withdrawn from the first treatment position and relocated to a nearby position without complete withdrawal from the incision. At the second position, additional treatment may be deployed. These last two steps may be repeated a number or times to provide complete treatment of the joint or joint region. Optionally, the needle 1 may be retracted partially or completely within the sleeve 3 while the device is relocated to reduce the risk of damage to tissues such as nearby neurovascular or cartilaginous structures during the relocation.

The needle 1 is preferably made of metal, more preferably stainless steel, but may be composed of a rigid plastic. The sleeve 3 may be made of many different materials that may be easily inserted into incisions and are able to be sterilized and packaged sterilely. Various types of rubber or plastic would be suitable and are known to those of skill in the art. The device may be made so that the base 4 fits in the sleeve 3 or, preferably, so that the base 4 slides over the sleeve 3 as the needle 1 is deployed.

As discussed above, the present invention includes one or more removable tabs 7. The tabs 7 may be molded as part of the base in such a manner that they can be readily broken off by the user at the proper time. Alternatively, they may be applied during manufacturing to the base or the sleeve in a removable manner. Alternatively, one or more tabs can be applied by the user prior to insertion to determine the exposure of the needle after the base is depressed. The tab(s) 7, if attached during manufacturing, should be stably attached so as to remain in place during packaging, shipping, and removal from the packaging, but be readily removable when it is time for the needle to be extended beyond the sleeve. The shape of a tab 7 is not important to the usefulness of the device of the present invention. It is only important that the tab is stably attached but removable when desired.

The length of the needle 1 extruding beyond the sleeve 3 may be varied by the number of tabs 7 that are removed. Thus, the use of multiple tabs 7 will make a particular embodiment of the present invention useful for different joints or different sizes of joints or different configurations of other tissues. If needed, a user could remove an additional tab or tabs during the procedure, so as to get a further extension of the needle if the situation requires it. Alternatively, a user could partially withdraw the base 4 from the sleeve 3 and replace or add a tab 7 during the procedure to change the length of the exposed needle 1.

The distal end of the sleeve 3 is preferably, but not necessarily, curved inward toward the needle 1 to facilitate insertion into the tissues. This will result in a rounded end having only a small opening for the extrusion of the needle 1 after insertion into the joint or cavity.

The proportions of the device can vary so that it is optimized for use in different joints. A device for use in an ankle, for example, would be shorter that one for the hip. Also the length of the base 4 can vary so that the device could have a longer exposed needle for reaching parts of a joint or surrounding tissue farther from the insertion point. The size can also vary to accommodate smaller or larger patients, for example a child or an obese adult, whose joints are farther from the insertion point.

Likewise, the diameter of the device can vary, particularly to accommodate different treatments. Growth factors and other biologicals are more viscous than anesthetics and would require a needle 1 with a larger lumen, such as a 12-14 gauge needle. Anesthetics or other less viscous treatments might only require a needle 1 that is 18-22 gauge.

The handle 8 is an optional part of the device but is preferred. It may be attached to the sleeve 3 or the base 4, preferably the base 4, to aid in placement of the device after insertion. It may be of any shape that is amenable for holding and directing the movement of the device. Preferably it has opposing positions for the thumb and forefinger to manipulate the device and facilitate rotation and is textured to facilitate the surgeon's grip on the device. It may be a separate piece attached by a fastening means or molded to the base 4 or the sleeve 3. Most preferably, it is an extension of the base 4. It may continue the curve of the device or be straight. It may be convex to aid in gripping. Optionally, the base 4 or the handle 8 may have an indicator to show the orientation of the curve of the sheath 3 and needle 1, which would be useful after insertion of the device to aid the user. The indicator may be a simple marking such as an arrow, or could be three dimensional and thus detectable by the user through touch. An example would be a raised button or bump 9 on the handle 8.

A connection means is located at the proximal end of the device of the present invention. Its purpose is to provide a means for attachment to the holder of the treatment (i.e., reservoir). A preferred example is a male or female luer taper (such as a BD Luer-Lok™ or BD Luer-Slip™ from Becton Dickinson). To the connection means, a reservoir, such as a syringe, preloaded with the treatment may be directly attached. Alternatively, and preferably, one end of an extension tube is connected to the connection means and, at the other end, the treatment reservoir. The reservoir (or extension tube and reservoir) may be connected prior to insertion of the device or may be connected after the device is in place and the needle has been extended.

The needle 1 can be optionally coated with a semi-rigid coating to reduce the risk of needle breakage and trauma to tissues from exposure to a metal needle. The coating can be composed of any material that is non-injurious to tissues and will adhere to the needle in a thin layer, but does not interfere with the movement of the needle 1 within the sleeve 3. The coating may also be chosen to reduce the friction between the needle 1 and the tissue. Alternatively, the coating may be chosen to aid in the closing of the needle track to prevent movement of the applied treatment outside its intended target. Examples include silicone substances and various plastics.

The needle 1 and sleeve 3 of the present invention are curved, but the curve may vary from low curvature to higher curvature. The degree of curvature can be chosen for the intended use. A low curvature may be desirable, for example, for a device intended for a saddle joint or another easily accessible cavity. A higher curvature may be desirable, for example, for a smaller joint or cavity or a ball and socket joint.

A preferred curve for an embodiment of the present invention intended for use in a ball and socket joint is between 20 and 30 degrees.

Treatments useful for pain relief are well known to those of ordinary skill in the art. Examples are benzocaine, butamben, dibucaine, lidocaine, oxybuprocaine, pramoxine, proparacaine, proxymetacaine, and tetracaine. They may be used singly or in combination. They may be used with or without epinephrine.

Platelet rich plasma (PRP) is a blood product with an increased concentration of platelets. PRP as well as other blood products and growth factors are increasingly being used in arthroscopic surgical procedures. In the future, stem cell products may be available that will work within joints or other cavities to repair cartilage, tendon, or other tissues. However, there is currently no safe, efficient, and effective way to deliver these products with precision to remote areas of joints. This device solves that problem by giving a surgeon the ability to precisely deliver PRP, blood products, growth factors, and other therapeutic products to the area being repaired.

All patents and publications referenced herein are incorporated by reference. The invention has been described in an illustrative manner, and it is to be understood that the terminology which has been used is intended to be in the nature of words of description rather than limitation. Obviously, many modifications and variations of the present invention are possible in light of the above teachings. It is, therefore, to be understood that within the scope of the appended claims, the invention may be practiced otherwise than a specifically described above.

The invention claimed is:

1. A medical device for injection of a treatment during endoscopy or arthroscopy, the device comprising a curved needle attached to the distal end of a base and surrounded by a curved sleeve; a connection means located at the proximal end of said base; at least one removable tab positioned so as to prevent movement of the base into the sleeve; and a stop to prevent the complete insertion of the base into the sleeve.

2. The medical device of claim 1 additionally comprising a handle useful for positioning the device.

3. The medical device of claim 1 wherein said stop is comprised of two external annular ridges, one on the base and one on the proximal end of the sleeve.

4. The medical device of claim 1 wherein said connection means is a luer taper.

5. The medical device of claim 1 wherein the number of tabs is 2 or greater.

6. The medical device of claim 1 wherein said needle is coated with a thin semi-rigid coating.

7. A medical device for injection of treatments during arthroscopy, the device comprising a curved needle attached to the distal end of a base and surrounded by a curved sleeve; a connection means located at the proximal end of said base; at least one removable tab positioned so as to temporarily prevent movement of the base into the sleeve; and a stop to prevent the complete insertion of the base into the sleeve; wherein said stop is an external annular ring on said base.

8. The medical device of claim 7 further comprising a handle.

* * * * *